US012599694B2

(12) United States Patent
Mofid

(10) Patent No.: US 12,599,694 B2
(45) Date of Patent: *Apr. 14, 2026

(54) SCAFFOLD WOUND DRESSING

(71) Applicant: Mehrdad Mark Mofid, San Diego, CA (US)

(72) Inventor: Mehrdad Mark Mofid, San Diego, CA (US)

(73) Assignee: SYLKE, INC., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/718,121

(22) Filed: Apr. 11, 2022

(65) Prior Publication Data

US 2022/0233742 A1     Jul. 28, 2022

Related U.S. Application Data

(63) Continuation of application No. 17/102,257, filed on Nov. 23, 2020, now Pat. No. 11,311,641, which is a continuation-in-part of application No. 17/100,675, filed on Nov. 20, 2020, now abandoned.

(51) Int. Cl.

| | |
|---|---|
| *A61L 15/32* | (2006.01) |
| *A61L 15/40* | (2006.01) |
| *A61L 15/58* | (2006.01) |

(52) U.S. Cl.
CPC ............... *A61L 15/32* (2013.01); *A61L 15/40* (2013.01); *A61L 15/58* (2013.01); *A61L 2300/64* (2013.01)

(58) Field of Classification Search
CPC ...... A61L 2300/64; A61L 15/40; A61L 15/58; A61L 15/32
See application file for complete search history.

(56) References Cited

U.S. PATENT DOCUMENTS

| | | | |
|---|---|---|---|
| 4,051,848 A | 10/1977 | Levine | |
| 6,048,806 A * | 4/2000 | Deeb | B32B 7/12 |
| | | | 442/151 |
| 6,087,546 A | 7/2000 | Griffiths et al. | |
| 6,175,053 B1 | 1/2001 | Tsubouchi | |
| 6,695,824 B2 | 2/2004 | Howard et al. | |
| 8,696,762 B2 | 4/2014 | Vogt et al. | |
| 9,750,838 B2 | 9/2017 | Duncan | |
| 10,039,721 B2 | 8/2018 | Bai | |
| 10,314,748 B2 | 6/2019 | Addison | |
| 10,398,800 B2 | 9/2019 | Jonn | |
| 10,648,109 B2 | 5/2020 | Mortarino et al. | |
| 11,311,641 B1 * | 4/2022 | Mofid | A61L 15/58 |
| 11,583,607 B2 * | 2/2023 | Mofid | A61L 15/425 |
| 2010/0227102 A1 | 9/2010 | Keener et al. | |
| 2012/0059300 A1 | 3/2012 | Ovington | |
| 2013/0101633 A1 | 4/2013 | Lowenhielm | |
| 2017/0014130 A1 * | 1/2017 | Patenaude | A61B 17/085 |
| 2017/0216478 A1 | 8/2017 | Lorenzoni | |

| | | | |
|---|---|---|---|
| 2018/0338945 A1 * | 11/2018 | Sambasivam | A61K 47/10 |
| 2022/0233742 A1 | 7/2022 | Mofid | |
| 2023/0226250 A1 * | 7/2023 | Mofid | A61L 15/32 |
| | | | 424/445 |

FOREIGN PATENT DOCUMENTS

| | | | |
|---|---|---|---|
| JP | 63179988 | 7/1988 | |
| JP | 2000502739 A | 3/2000 | |
| KR | 20040011786 A | 2/2004 | |
| WO | 2012151151 A1 | 11/2012 | |
| WO | WO-2019040850 A1 * | 2/2019 | A61K 33/244 |

OTHER PUBLICATIONS

Brian P. Sautter, Continuous Polymer Nanofibers Using Electrospinning, Aug. 5, 2005, NSF-REU, Department of Mechanical Engineering (Year: 2005).*
Yongjie Jiao, Construction and application of textile-based tissue engineering scaffolds: a review, May 23, 2020, Biomater. Sci. 8, 3574-3600 (Year: 2020).*
Yu Suzuki, Structures of silk fibroin before and after spinning and biomedical applications, 2016, Polymer Journal, 48, 1039-1044 (Year: 2016).*
Murad Karadsheh, Application of a Skin Adhesive to Maintain Seal in Negative Pressure Wound Therapy: Demonstration of a New Technique, 2017, Wounds, 29(11); E106-E110, https://www.woundsresearch.com/article/application-skin-adhesive-maintain-seal-negative-pressure-wound-therapy-demonstration-new (Year: 2017).*
Stoica, et al., "Nanomaterials for Wound Dressing: An Up-to-Date Overview," Molecules 2020, 25, 2699, 25 pages.
Kim, et al., "Rapidly photocurable silk fibroin sealant for clinical applications," NPG Asia Materials (2020) 12:46.
Sambri et al., "In vitro evaluation of the bio-activity of different fabrics for underwear against . . . ," First Presentation, FAACI 2009 Warszawa, Jun. 6-10, 2009, 4 pages.

(Continued)

*Primary Examiner* — Sue X Liu
*Assistant Examiner* — Ali S Saeed
(74) *Attorney, Agent, or Firm* — Pillsbury Winthrop Shaw Pittman LLP

(57) ABSTRACT

Disclosed is an external wound dressing formed of a bioprotein scaffolding that may include a pressure-sensitive adhesive impregnated in the bioprotein scaffolding. A method of wound treatment can include adhering an external wound dressing formed of a bioprotein scaffolding to an external injury site. Another method can include applying an adhesive to the skin of a patient, placing an external wound dressing formed of a bioprotein scaffolding over an injury site on the skin of the patient, and applying a sealing adhesive on top of the bioprotein scaffolding. Yet another method can include applying an adhesive to the skin of a patient, placing an external wound dressing formed of a bioprotein scaffolding over an injury site on the skin of the patient that has not been stitched, and applying a sealing adhesive on top of the bioprotein scaffolding.

14 Claims, 4 Drawing Sheets

(56) References Cited

OTHER PUBLICATIONS

M. Mark Mofid, MD, FACS, et al., "Circumareolar Mastopexy With SERI® Surgical Scaff old Reinforcement," Quality Medical Publishing, Feb. 10, 2015, https://www.qmp.com/pulse/article/55.

Eloquest Healthcare, Mastisol Liquid Adhesive, Sep. 22, 2020, Eloquest Healthcare, https://eloquesthealthcare.com/mastisol/#:-:text=Mastisol%20is%20a%20liquid%20medical%20adhesive%20used%2oto,with%20reduced%2otime%20associated%20with%20unplanned%20dressing%20changes.%E2%81%B8 (Year: 2020).

John Joseph, Transforming Nanofibers into Woven Nanotextiles for Vascular Application, May 24, 2018, ACS Applied Materials & Interfaces, 10, 19449-19458 (Year: 2018).

Senti et al, "Antimicrobial Silk Clothing in the Treatment of Atopic Dermatitis Proves Comparable to Topical Corticosteroid Treatment," Dermatology 2006; 213:228-233, Feb. 2, 2006, 6 pages.

* cited by examiner

110

210

220

SCAFFOLD WOUND DRESSING

RELATED APPLICATION(S)

This application is a continuation of and claims priority to and the benefit of U.S. patent application No. 17/102,257, filed Nov. 23, 2020, titled "Scaffold Wound Dressing," which is a continuation-in-part of U.S. patent application No. 17/100,675, filed Nov. 20, 2020, titled "Scaffold Wound Dressing," the contents of each are hereby incorporated by reference.

DESCRIPTION OF THE RELATED ART

Wound care can include the use of dressings and other products used to support healing, for example, by covering wounds to help keep them clean and by partially immobilizing or supporting wounded skin in order to facilitate healing. Common wound dressing methods include the use of adhesive tape (e.g., Steri-Strips), glues, gauze, synthetic meshes, etc. However, present dressing products and methods have high rates of contact dermatitis, skin blistering, poor adherence in the presence of water and bathing, difficulty with removal, and other shortcomings.

SUMMARY

The present disclosure includes, for example, a wound dressing that may be formed of a bioprotein scaffolding and include a pressure-sensitive adhesive impregnated in the bioprotein scaffolding. The bioprotein scaffolding may be formed of bioprotein fibers woven together to form regular or semi-regular boundaries of interstitial spaces. The pressure-sensitive adhesive may also be configured to avoid leaving a residue when the bioprotein scaffolding is removed from a patient.

In a related aspect, a method of wound treatment can include adhering an external wound dressing formed of an animal-derived bioprotein scaffolding to an external injury site on the skin of a patient, such as a surgical incision. An adhesive can first be applied to the skin of the patient around an injury site, the external wound dressing formed of an animal-derived bioprotein scaffolding can be placed on the adhesive, and an additional sealing adhesive can be applied on top of the bioprotein scaffolding.

In another aspect, a method of wound treatment can include applying an adhesive to skin of a patient, placing an external wound dressing formed of a bioprotein scaffolding over an injury site on the skin of the patient that has not been stitched, and applying a sealing adhesive on top of the bioprotein scaffolding.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

The present disclosure includes apparatuses, methods and kits for facilitating wound healing that are especially beneficial for dressing closed surgical incisions and cut wounds that may or may not have been sutured. Included in this disclosure are novel external wound dressing products, for example, scaffoldings including pressure-sensitive adhesives, which can be easily affixed to wounds to prevent wound/incisional separation. Also disclosed are novel methods for external wound dressing that utilize a bioprotein scaffolding on an external injury site, which may be affixed with an adhesive and may also be further coated with a water-resistant sealing adhesive.

Figure 1:
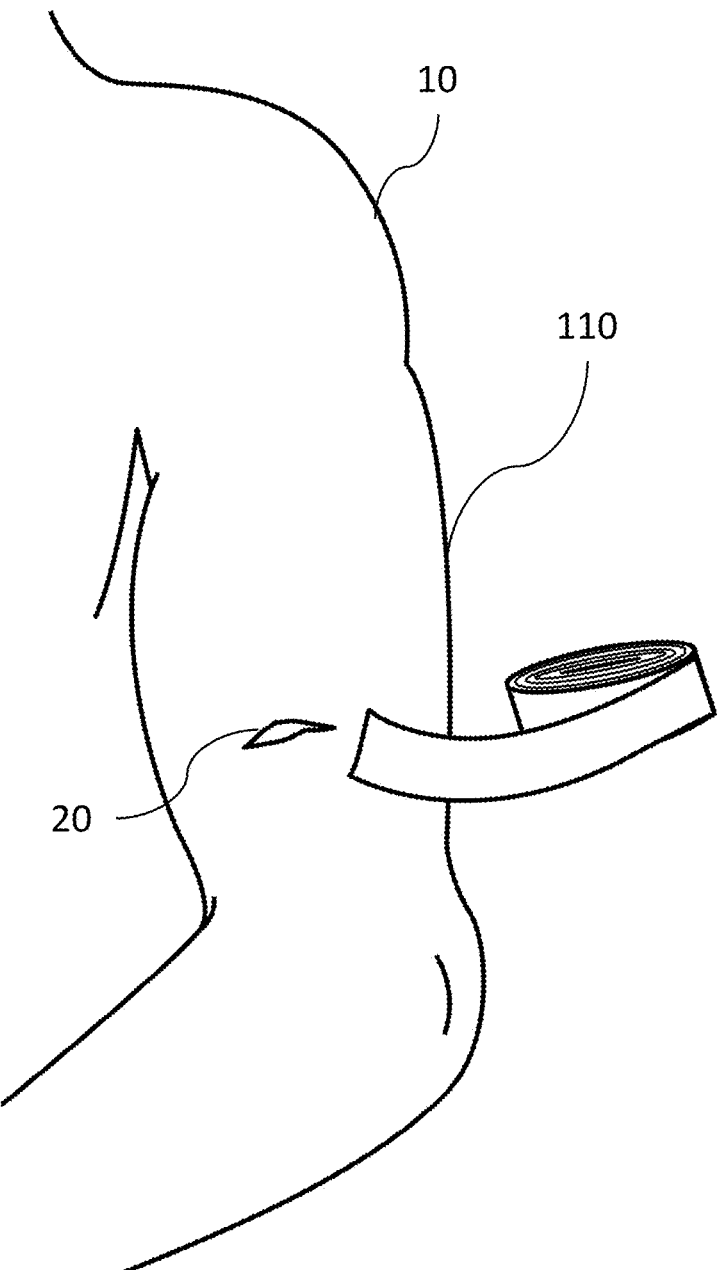
FIG. 1 is a diagram illustrating an exemplary external wound dressing being affixed to a patient in accordance with certain aspects of the present disclosure.

FIG. 1 is a diagram illustrating an exemplary external wound dressing 110 for affixing to a patient 10 having a wound 20. An apparatus for facilitating wound closure and healing (often referred to herein as an external wound dressing) may, for example, be formed of a bioprotein scaffolding and a pressure-sensitive adhesive (PSA) impregnated in the bioprotein scaffolding. Such a bioprotein scaffolding may be formed into a roll (as shown in FIG. 1) from which specific-sized portions may be cut. Alternatively, the external wound dressing may be provided as individual sheets from which portions may be cut, or one or more precut pieces appropriate for a particular use (e.g., small pieces for small wounds and larger pieces for large wounds).

As used herein, the term "impregnated" (e.g., a pressure-sensitive adhesive "impregnated" in the bioprotein scaffolding) refers to any addition (e.g., of an adhesive) to the bioprotein scaffolding. The addition can be in the form of one or more layers of adhesive on the surface of the bioprotein scaffolding, the inclusion of an adhesive into the structure of the strands themselves (e.g., absorbed, saturated, or otherwise included inside the bioprotein scaffolding strands), the inclusion of adhesive within interstitial spaces of the scaffolding, or any combination of the above. The term "integrated" is also used in certain locations in the present disclosure (e.g., the bioprotein scaffolding with "integrated" adhesive) and such should be considered synonymous with the term "impregnated," as described above.

In certain embodiments, an external wound dressing can be formed from a bioprotein derived from living organisms. Examples of bioproteins can include silk, cotton, porcine dermis, small intestine submucosa and bovine dermis or pericardium. In some embodiments, the external wound dressings contemplated herein can be formed specifically of one or more animal-derived bioproteins. In other embodiments, the external wound dressings may be formed more specifically of insect-derived bioproteins, for example, from spiders. In one particular embodiment, the bioprotein scaffolding can include a silk bioprotein, such as can be obtained, for example, from Bombyx mori silkworms. Other types of silk (and their silkworm sources) can include Muga (Antheraea assamensis silkworm), Eri (Sarnia cynthia ricini silkworm), or Pat (Bombyx textor silkworm). The use of such bioproteins can reduce or prevent contact dermatitis or allergic reactions that can occur with some synthetics.

As used herein, the term "bioprotein" includes any organic (i.e., not synthetic) material. When embodiments are described herein as being formed of a bioprotein material (e.g., external wound dressings formed of a bioprotein scaffolding, an animal- derived bioprotein scaffolding, an insect-derived bioprotein scaffolding, or a silk bioprotein scaffolding), such is intended to mean formed primarily of organic material, and the inclusion of a portion of non-bioprotein material is contemplated. Thus, bioprotein products as disclosed herein include dressings that are at least 50% bioprotein, but may also be substantially (i.e., more than 90%, 95%, 99%, or even essentially 100%) bioprotein.

In some embodiments, silk bioproteins can be processed in order to have a reduced amount of sericin relative to the amount of sericin naturally present in the silk bioprotein (raw silk fibers are composed of fibroin protein core filaments that are naturally coated with the globular protein sericin). Some implementations of the disclosed external wound dressings can include having silk fibers where sericin is extracted from the fiber, leaving behind fibroin protein with minimal residual sericin. This extraction or purification of the fibers can result in silk fibers being at least 80% fibroin protein with 20% or less of the sericin remaining. In another exemplary embodiment, the extraction can result in silk fibers having at least 95% fibroin protein with 5% or less sericin remaining.

Figure 2:
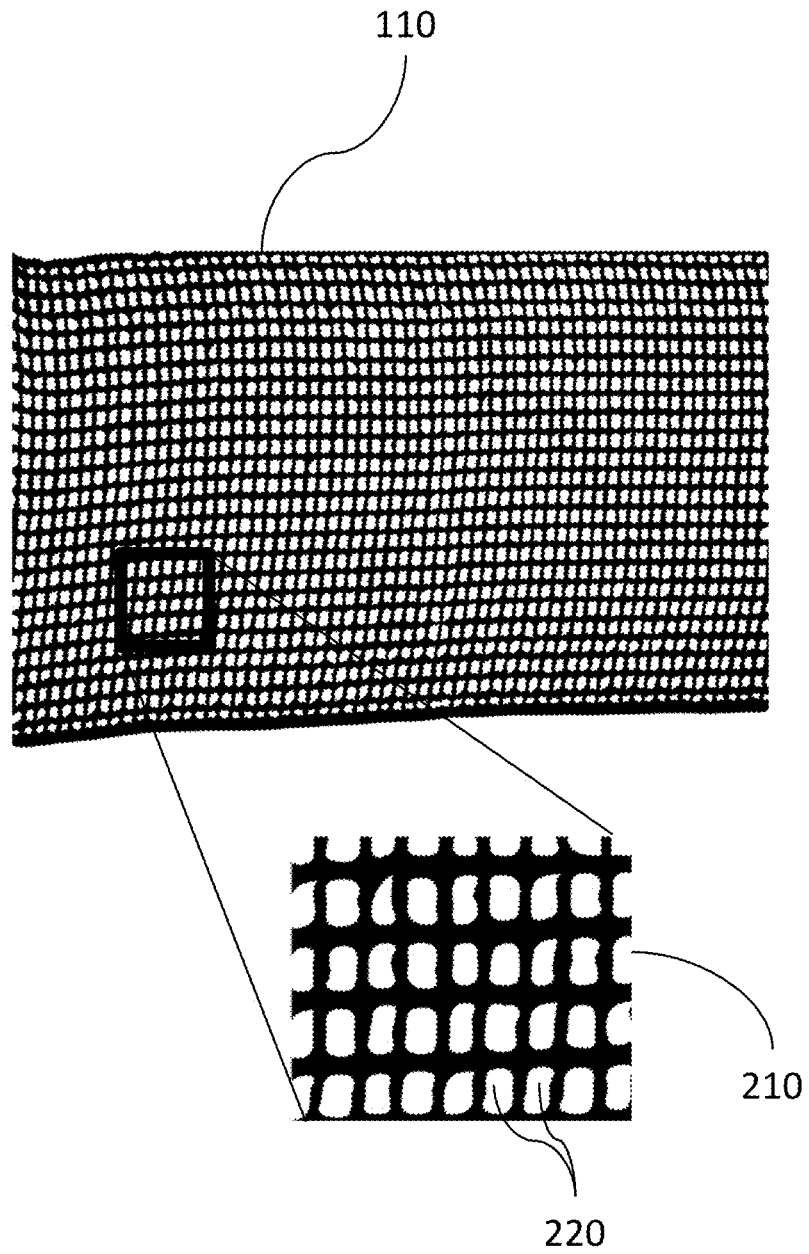
FIG. 2 is a simplified diagram illustrating an exemplary external wound dressing, depicting its scaffolding structure in accordance with certain aspects of the present disclosure.

FIG. 2 is a simplified diagram illustrating an exemplary external wound dressing depicting a scaffolding structure. A section of the external wound dressing 110 is depicted in FIG. 2 as a flexible portion having a scaffolding structure such that there are interstitial spaces between the strands that make up the external wound dressing.

The scaffolding aspect of the external wound dressing is more easily seen in the enlarged portion 210 of external wound dressing 110. The scaffolding structure of the external wound dressing can be formed as woven or knitted strands of bioprotein fibers and referred to herein as "bioprotein scaffolding." In one exemplary embodiment, the fibers may be generally straight, with the threads parallel to an elongate direction of the dressing being called "warp threads" or perpendicular "weft threads." The fibers may follow a meandering path "a course" and be arranged in loops "bights" that extend above and below the path of the course. A sequence of stitches in which stitches are intertwined and locked with the next "a wale" resists the knitted fiber from being undone. As used herein, knitted and woven are assumed to be substantial equivalents in terms of the scaffolding (i.e., the scaffolding may be alternatively described as either "knitted" or "woven").

As shown in FIG. 2, some embodiments of the bioprotein scaffolding can include strands of bioprotein fibers woven together to form regular or semi-regular boundaries of interstitial spaces 220. As used herein, the term "regular " means that the shape of the boundary substantially repeats. For example, regular boundaries can define substantially rectangular interstitial spaces that epeat to form a substantially homogenous scaffolding structure. These "regular"

boundaries can have an area or dimension that varies by, e.g., no more: than 5% and can generally have the same local shape (e.g., squares). When referring to "semiregular boundaries," these may vary by, e.g., no more than 20% but may differ in shape locally (e.g., squares adjacent to rectangles).

In some implementations, the strands of bioprotein fibers comprise multiple silk protein filaments that are combined by helical twisting to form a multifilament bioprotein. fiber. These strands are then woven to form the scaffolding having interstitial spaces described above. The size of the interstitial spaces can vary. In one embodiment, the area of the interstitial spaces can be approximately 0.1 mm2 (e.g., 0.08 to 0.12 mm2). Other implementations can include interstitial spaces being between 0.01 and 0.1 mm2 or between 0.1 and 0.5 mm2, etc. One example of such a scaffolding is the SERI® Surgical Scaffold Silk produced by Sofregen Medical, Inc.

The present disclosure further contemplates the use of synthetic scaffolding products in certain embodiments. The synthetic scaffolding may have characteristics similar to the bioprotein scaffolding described herein (e.g., be similarly woven, have similar interstitial spaces, etc.) but be formed of a synthetic material such as polyester, rayon, or other material rather than a bioprotein. Such synthetic scaffoldings can also incorporate the use of any of the adhesives as described herein (e.g., the present disclosure contemplates the use of a synthetic scaffolding with a pressure-sensitive adhesive).

To allow for adhesion to an external surface (e.g., to a patient's skin), in some embodiments, an external wound dressing can be formed of a bioprotein scaffolding with a pressure-sensitive adhesive impregnated in the bioprotein scaffolding. As previously mentioned, the bioprotein scaffolding can have an outside layer containing the PSA, or may have the PSA distributed within the scaffolding structure itself (e.g., within or between strands) such that the application of the bioprotein scaffolding to the patient causes the PSA to form an adhesive bond between the bioprotein scaffolding and the patient.

One exemplary implementation can include utilizing such bioprotein scaffoldings instead of surgical stitches or staples. In implementations where the bioprotein scaffolding is impregnated with pressure-sensitive adhesive, the addition of further adhesive may not be required and the PSA-impregnated bioprotein scaffolding itself may be sufficient to securely retain closure of the wound.

As used herein, "pressure-sensitive adhesive" (PSA) refers to an adhesive that forms a bond when pressure is applied, in order to bond the adhesive with a surface. No solvent, water, or heat is needed to activate the adhesive (similar to the adhesive used in conjunction with Post-it® notes or Post-it® Extreme notes). As the name "pressure-sensitive" indicates, the degree of bond may be influenced by the amount of pressure that is used to apply the adhesive to the surface. Surface factors such as smoothness, surface energy, removal of contaminants, etc., can also be important to proper bonding.

In some embodiments, the PSA can be formed of tacky, elastomeric polymers. They may be comprised of be small spheres (microspheres) and generally insoluble. The microspheres can have diameters in the range of 1 to 250 microns with most being 5 to 150 microns. These polymers can easily bond to desired surfaces, such as a patient's skin. The adhesive can be essentially of 90 to about 99.5 percent by weight of at least one alkyl acrylate ester and 10 to 0.5 percent by weight of substantially oil-insoluble, water-soluble, ionic monomers and maleic anhydride. In some embodiments, the microspheres can be 95 to 99 percent by weight acrylate monomer and 5 to 1 percent by weight ionic monomer, maleic anhydride, or a mixture thereof.

Specifically, the adhesive can include alkyl acrylate monomers, such as iso-octyl acrylate, 4-methyl-2-pentyl acrylate, 2-methylbutyl acrylate, sec-butyl acrylate, etc. The water-soluble ionic monomer portion of these microspheres can include monomers which are substantially insoluble in oil, for example, those with a solubility of less than 0.5% by weight. They may also have a distribution ratio at a given temperature (preferably 50° - 65° C.) of solubility in the oil phase monomer to solubility in the aqueous phase of less than 0.005. Examples of ionic monomers can include sodium methacrylate, ammonium acrylate, sodium acrylate, etc. Chemical formulas for such PSAs can include Aqueous 98:2 n-butylacylate:hdroxy-methacrylate emulsion, Aqueous 92:4:3:1 isooctylacrylate:acrylic acid:methyl methacrylate:styrene emulsion, 10% heptane solution of 95.5:4.5 isooctyl acrylate:acrylic acid copolymer, etc.

The adhesive can be produced by aqueous suspension polymerization incorporating an emulsifier in an amount exceeding the critical micelle concentration without additional colloids. The microspheres forming the pressure-sensitive adhesive can have a low adhesion that allows ease of removal and re-application and can have a tensile strength of, for example, less than 10psi.

Other embodiments can include the incorporation of waterproof pressure- sensitive adhesives (WPSAs) similar to the PSAs described above but with additional waterproofing features (e.g., the adhesive used in conjunction with Post-it® Extreme notes/acrylic based adhesives that resist dissolving or otherwise losing adhesive strength in the presence of vapor or water). As used herein, the term "waterproof" refers to the ability of the adhesive (or the adhesive-using product) to retain its function when exposed to water, sweat, etc. The term "waterproof" encompasses adhesives that are completely waterproof or merely water-resistant. For example, WPSAs may lose some adhesion in the presence of water while still adhering better than would general PSAs. As such, WPSAs may be able to retain adhesion after a finite number of showers, baths, pool/swimming immersions, periods of vigorous exercise, etc.

The present disclosure contemplates that a scaffolding impregnated with a waterproof pressure-sensitive adhesive could be used as a waterproof wound dressing without the need for the application of any additional sealing adhesive.

In some embodiments, the pressure-sensitive adhesive may also be configured to avoid leaving behind a residue when the bioprotein scaffolding is removed from a patient. Such implementations can include use of PSAs or WPSAs that may be acrylate PSAs or rubber or silicone-based adhesives. In addition to having generally lower cohesive strength than other adhesives that tend to leave residue, such formulations of pressure-sensitive adhesives can benefit from having a lack of materials that often form a residue, for example, plasticizer, oil, the former, or low-molecular weight polymer that can migrate to the surface of the adhesive.

Figure 3:
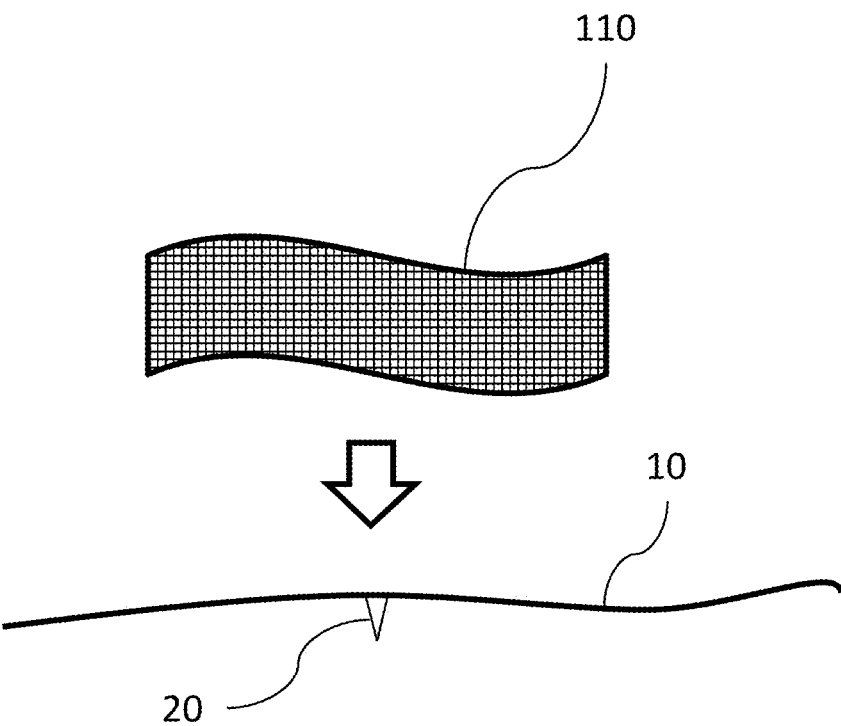
FIG. 3 is a simplified diagram depicting application of an external wound dressing impregnated with an adhesive in accordance with certain aspects of the present disclosure.

FIG. 3 is a simplified diagram depicting application of an external wound dressing 110 that is impregnated with an adhesive. One method of application can include adhering an external wound dressing formed of a bioprotein scaffolding (e.g., any of the types of bioprotein scaffoldings described above) to an external injury site. External injury sites can be on the skin of a patient (such as a minor to moderate cut), a surgical incision, etc.

As described above, an adhesive (e.g., a gum resin or PSA) can be integrated with the bioprotein scaffolding. Accordingly, adhering the bioprotein scaffolding can include application of the bioprotein scaffolding with the integrated adhesive, for example, to an external wound of the patient. in some implementations, the adhesive can be a PSA Aqueous 98:2 n-butylacrylate:hydroxy-methacrylate emulsion), which may also be configured to avoid leaving a residue on the patient when the bioprotein scaffolding is removed.

Figure 4:
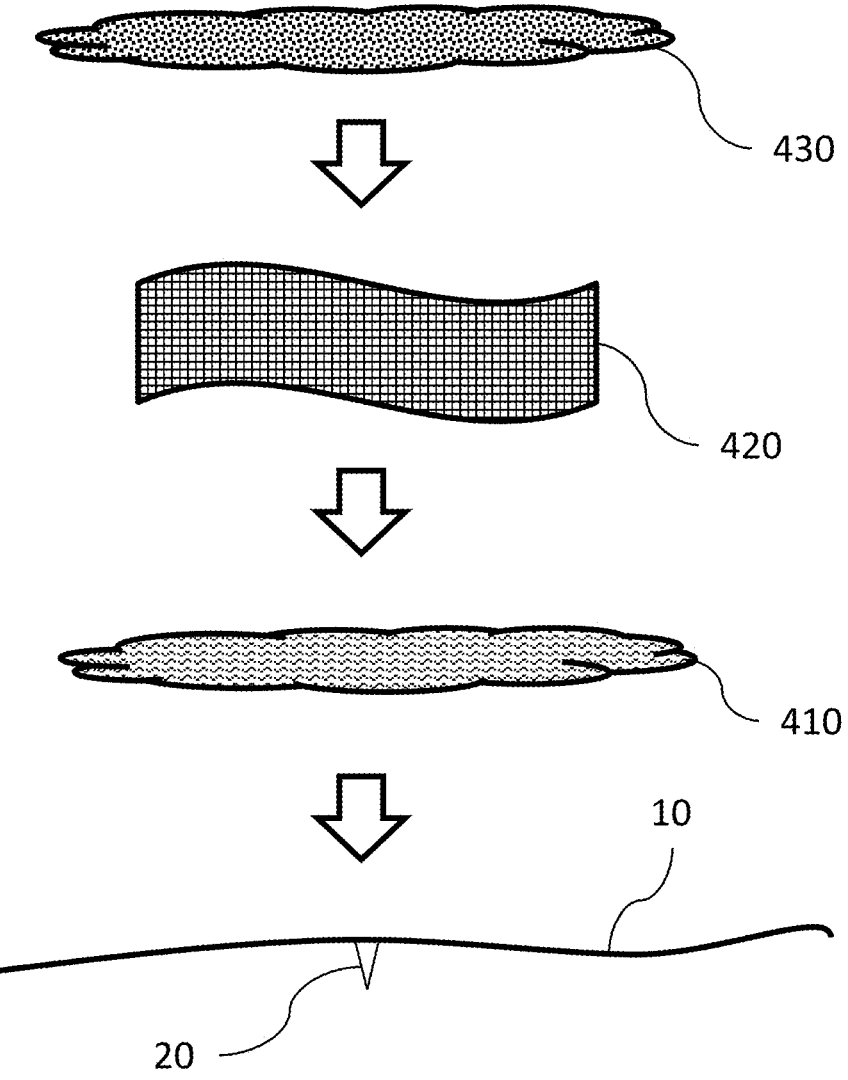
FIG. 4 is a simplified diagram depicting application of an adhesive, followed by application of an external wound dressing, and finally application of a sealing adhesive in accordance with certain aspects of the present disclosure.

FIG. 4 is a simplified diagram depicting alternative methods of use, for example, with scaffoldings that do not have an integrated adhesive. In such cases, the adhering can include application of an adhesive 410 to a patient followed by application of the bioprotein scaffolding 420 (e.g., any of the types of bioprotein scaffoldings described above). The scaffolding could also be applied before the adhesive, however, applying the adhesive first is typically preferable. The adhesive 410 may be, for example, a gum resin, a PSA, a WPSA, etc.

As shown in FIG. 4, waterproofing can be enabled by optionally applying a sealing adhesive 430 (e.g., one including cyanoacrylate) on top of the bioprotein scaffolding. The sealing adhesive can be applied after the base adhesive has dried sufficiently, which typically takes only a few seconds. Such waterproofing can permit the patient to more easily shower or swim without the concern that the external wound dressing will fall off and expose the wound site to bacteria.

The present disclosure also contemplates methods wherein a sealing adhesive 430 may be applied over a scaffolding that has an integrated adhesive (especially if the adhesive is not itself waterproof).

In any of the disclosed embodiments, the method of adhering could alternatively include application of a tape over the bioprotein scaffolding. Furthermore, the methods described herein may also include cutting the external wound dressing from a larger portion of external wound dressing (e.g., from a roll of external wound dressing as shown in FIG. 1).

The improvements of the disclosed external wound dressings and methods can provide a strong and flexible dressing such that, in some cases, stitching may not be required, thus improving patient healing and reducing the work of medical practitioners. Thus, another alternative method can include applying an adhesive to the skin of a patient, placing an external wound dressing formed of a bioprotein scaffolding (e.g., any of the types of bioprotein scaffoldings described above) over an injury site on the skin of the patient (e.g., one that has not been stitched), and applying a sealing adhesive on top of the bioprotein scaffolding.

The present disclosure also contemplates kits of products that may be sold together and may include any of the disclosed products in any combination to perform any of the methods described herein. One such kit may include an external wound dressing formed of a bioprotein scaffolding, an adhesive such as a gum resin, and a sealing adhesive such as a cyanoacrylate-based adhesive. Another kit may include a dressing formed of a scaffolding impregnated with a pressure-sensitive adhesive or a waterproof pressure-sensitive adhesive, along with a sealing adhesive. Another kit can include a scaffolding as described above with a pressure-sensitive adhesive or waterproof pressure-sensitive adhesive as a separate item, as well as a separate sealing adhesive. In various kits, instructions can be included to explain any of the methods of use disclosed herein.

In the following, further features, characteristics, and exemplary technical solutions of the present disclosure will be described in terms of items that may be optionally claimed in any combination:

Item 1: A method comprising adhering an external wound dressing formed of an animal-derived bioprotein scaffolding to an external injury site.

Item 2: A method comprising: applying an adhesive to skin of a patient; placing an external wound dressing formed of a bioprotein scaffolding over an injury site on the skin of the patient; and applying a sealing adhesive on top of the bioprotein scaffolding.

Item 3: A method comprising: applying an adhesive to skin of a patient; placing an external wound dressing formed of a bioprotein scaffolding over an injury site on the skin of the patient that has not been stitched; and applying a sealing adhesive on top of the bioprotein scaffolding.

Item 4: A method as in any of the preceding Items, wherein the external injury site is on the skin of a patient.

Item 5: A method as in any of the preceding Items, wherein the animal-derived bioprotein scaffolding comprises an insect-derived bioprotein.

Item 6: A method as in any of the preceding Items, wherein the animal-derived bioprotein scaffolding comprises a silk bioprotein.

Item 7: A method as in any of the preceding Items, wherein the silk bioprotein is obtained from Bombyx mori silkworms.

Item 8: A method as in any of the preceding Items, wherein the silk bioprotein has a reduced amount of sericin relative to the amount of sericin naturally present in the silk bioprotein.

Item 9: A method as in any of the preceding Items, wherein the animal-derived bioprotein scaffolding is woven.

Item 10: A method as in any of the preceding Items, wherein the animal-derived bioprotein scaffolding is formed of bioprotein fibers woven together to form regular or semi-regular boundaries of interstitial spaces.

Item 11: A method as in any of the preceding Items, wherein the adhering comprises application of an adhesive to a patient followed by application of the bioprotein scaffolding.

Item 12: A method as in any of the preceding Items, wherein an adhesive is integrated with the bioprotein scaffolding and the adhering comprises application of the bioprotein scaffolding with the integrated adhesive.

Item 13: A method as in any of the preceding Items, wherein the adhesive is a gum resin.

Item 14: A method as in any of the preceding Items, wherein the adhesive is a pressure-sensitive adhesive.

Item 15: A method as in any of the preceding Items, wherein the adhesive is configured to avoid leaving a residue on the patient when the animal-derived bioprotein scaffolding is removed.

Item 16: A method as in any of the preceding Items, further comprising applying a sealing adhesive on top of the bioprotein scaffolding.

Item 17: A method as in any of the preceding Items, wherein the sealing adhesive comprises cyanoacrylate.

Item 18: A method as in any of the preceding Items, wherein the bioprotein scaffolding comprises an animal-derived bioprotein.

Item 19: An apparatus comprising an external wound dressing formed of a bioprotein scaffolding; and a pressure-sensitive adhesive impregnated in the bioprotein scaffolding.

Item 20: An apparatus as in Item 19, wherein the pressure-sensitive adhesive is configured to avoid leaving a residue when the bioprotein scaffolding is removed from a patient.

Item 21: An apparatus as in any of Items 19-20, wherein the pressure-sensitive adhesive is Aqueous 98:2 n-butylacrylate:hydroxy-methacrylate emulsion.

Item 22: An apparatus as in any of Items 19-21, wherein the bioprotein scaffolding comprises an animal-derived bioprotein.

Item 23: An apparatus as in any of Items 19-22, wherein the bioprotein scaffolding comprises an insect-derived bioprotein.

Item 24: An apparatus as in any of Items 19-23, wherein the bioprotein scaffolding comprises a silk bioprotein.

Item 25: An apparatus as in any of Items 19-24, wherein the silk bioprotein is obtained from Bombyx mori silkworms.

Item 26: An apparatus as in any of Items 19-25, wherein the silk bioprotein has a reduced amount of sericin relative to the amount of sericin naturally present in the silk bioprotein.

Item 27: An apparatus as in any of Items 19-26, wherein the bioprotein scaffolding is woven.

Item 28: An apparatus as in any of Items 19-27, wherein the bioprotein scaffolding is formed of bioprotein fibers woven together to form regular or semi-regular boundaries of interstitial spaces.

Item 29: An apparatus as in any of Items 19-28, wherein the bioprotein scaffolding comprises a roll from which specific-sized portions may be cut.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, kits and/or articles depending on the desired configuration. Any methods or logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all noted advantages.

Additionally, section headings shall not limit or characterize the invention(s) set out in any claims that may issue from this disclosure. Further, the description of a technology in the "Description of Related Art" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. An apparatus comprising:
an external wound dressing configured to be adhered to skin over a wound and to prevent wound separation, the external wound dressing formed of an animal-derived bioprotein scaffolding of sufficient strength to prevent wound separation, wherein the animal-derived bioprotein scaffolding consists of bioprotein fibers woven together to form regular or semi-regular boundaries of interstitial spaces, and a pressure-sensitive adhesive impregnated in the bioprotein scaffolding for directly adhering the animal-derived bioprotein scaffolding to the skin to prevent wound separation.

2. The apparatus of claim 1, wherein the bioprotein fibers are an insect-derived bioprotein.

3. The apparatus of claim 2, wherein the bioprotein fibers are a silk bioprotein.

4. The apparatus of claim 3, wherein the silk bioprotein is obtained from Bombyx mori silkworms.

5. The apparatus of claim 4, wherein the silk bioprotein has a reduced amount of sericin relative to the amount of sericin naturally present in the silk bioprotein.

6. The apparatus of claim 1, wherein the adhesive is included within the interstitial spaces.

7. The apparatus of claim 1, further comprising a sealing adhesive on top of the animal-derived bioprotein scaffolding.

8. The apparatus of claim 7, wherein the sealing adhesive comprises cyanoacrylate.

9. The apparatus of claim 1, wherein the bioprotein fibers are multiple silk protein filaments combined by helical twisting to form a multi-filament bioprotein fiber.

10. The apparatus of claim 1, wherein the boundaries of the interstitial spaces have an area or dimension that varies by no more than 5%.

11. The apparatus of claim 1, wherein the boundaries of the interstitial spaces have an area or dimension that varies by no more than 20%.

12. The apparatus of claim 1, wherein the pressure-sensitive adhesive is an Aqueous 98:2 n-butylacrylate: hydroxy-methacrylate emulsion.

13. The apparatus of claim 1, wherein the bioprotein scaffolding is formed into a roll from which specific-sized portions may be cut.

14. The apparatus of claim 1, wherein the pressure-sensitive adhesive is an acrylic material making the pressure-sensitive adhesive a waterproof pressure sensitive adhesive that causes the external wound dressing to retain more adhesion in the presence of water than a non-waterproof pressure-sensitive adhesive.

* * * * *